(12) United States Patent
Wu et al.

(10) Patent No.: US 7,871,269 B2
(45) Date of Patent: Jan. 18, 2011

(54) INJECTION IMPRESSION TRAY

(75) Inventors: Ken Wu, San Francisco, CA (US); Jon Moss, Antioch, CA (US); Ryan Kimura, San Jose, CA (US); Heng Cao, Sunnyvale, CA (US)

(73) Assignee: Align Technology, Inc., San Jose, CA (US)

( * ) Notice: Subject to any disclaimer, the term of this patent is extended or adjusted under 35 U.S.C. 154(b) by 117 days.

(21) Appl. No.: 11/867,608

(22) Filed: Oct. 4, 2007

(65) Prior Publication Data

US 2009/0092942 A1    Apr. 9, 2009

(51) Int. Cl.
*A61C 9/00*    (2006.01)

(52) U.S. Cl. .............................. 433/214; 433/36; 433/37

(58) Field of Classification Search .................... 433/34, 433/35, 36, 37, 38, 41, 42, 45, 47, 214
See application file for complete search history.

(56) References Cited

U.S. PATENT DOCUMENTS

| | | | |
|---|---|---|---|
| 2,155,334 A | 4/1939 | Sitkin et al. | |
| 3,211,149 A | 10/1965 | Fono | |
| 3,357,104 A | 12/1967 | Greene et al. | |
| 3,722,097 A | 3/1973 | Colman et al. | |
| 4,375,965 A | 3/1983 | Weissman | |
| 4,378,211 A | 3/1983 | Lococo | |
| 4,382,785 A | 5/1983 | Lococo | |
| 4,652,237 A * | 3/1987 | Cills | 433/37 |
| 5,370,533 A * | 12/1994 | Bushnell | 433/36 |
| 5,890,895 A * | 4/1999 | Tucker | 433/37 |
| 5,975,893 A | 11/1999 | Chishti et al. | |
| 6,394,802 B1 * | 5/2002 | Hahn | 433/37 |
| 6,398,550 B1 * | 6/2002 | Caritg | 433/37 |
| 6,450,807 B1 | 9/2002 | Chishti et al. | |
| 6,758,671 B2 | 7/2004 | Brattesani | |

\* cited by examiner

*Primary Examiner*—Cris L Rodriguez
*Assistant Examiner*—Michael R Ballinger
(74) *Attorney, Agent, or Firm*—Townsend and Townsend and Crew LLP

(57) ABSTRACT

The present invention relates to an improved dental impression tray and related methods. In one embodiment, a dental impression tray includes a first portion for receiving impression material from a source and a second portion is configured for receiving a patient's upper or lower teeth and will at least partial define a cavity shaped to receive the teeth during use. In use, impression material introduced into the first portion can pass through openings and into the second portion and around a patient's teeth.

24 Claims, 4 Drawing Sheets

INJECTION IMPRESSION TRAY

BACKGROUND OF THE INVENTION

The present invention relates generally to dental impression trays, and more particularly to improved dental impression trays for more evenly and efficiently flooding impression material into the tray and around teeth positioned in the tray.

In the fields of dentistry and orthodontics, a wide variety of procedures and techniques require fabricating a model of a patient's teeth. Modeling teeth often requires making accurate castings of a patient's teeth, tooth surfaces, gingival and other fine details of the patient's dentition. Traditional dental castings are made by loading a dental impression tray or shell with a liquid dental impression material, which is generally a viscous and quick setting material that must be quickly applied to the patient's teeth soon after mixing. The tray loaded with impression material is then inserted into a patient's mouth, and the patient closes their mouth in order to hold the tray in position until the impression material has sufficiently solidified. After the material has solidified sufficiently, the tray and impression material are removed, with the solidified material containing an impression of the dental surfaces of the patient.

One problem with existing impression trays lies in the need to load it with impression material and then seat it in the patient's mouth. Loading the tray typically includes layering a thick bead of impression material into a teeth receiving cavity of the tray, e.g., by extruding material from a cartridge gun into the tray cavity. This loading process often results in the encapsulation of air bubbles/pockets if the beads are not correctly extruded, which when applied onto the patient, will produce an inaccurate impression with missing anatomy. Additionally, accurately seating a fully loaded impression tray onto the teeth is difficult and can include misalignment during or after insertion. If the tray is improperly placed or is accidentally shifted during the setting time, the resulting impression will be distorted. Further, as a fully loaded tray has to be applied with a substantial (and uncomfortable) amount of force, such force may displace the impression material out of the tray to create a shallow model and show through as the target anatomy enters the confines of the interior tray cavity.

Recent advances in dentistry and orthodontics has increased the value and need for obtaining accurate, higher quality impressions of patients' teeth. In the field of orthodontics, for example, both traditional orthodontics as well as alternatives to conventional orthodontic treatment with traditional affixed appliances often make use of impressions of a patient's teeth, and as technology progresses higher quality impressions are becoming even more desired. For example, systems including a series of preformed aligners have become commercially available from Align Technology, Inc., Santa Clara, Calif., under the tradename Invisalign® System. The Invisalign® System includes designing and/or fabricating multiple aligners to be sequentially worn by the patient in order to reposition the teeth over time. Often, designing and planning a customized treatment for a patient, as well as administration and monitoring of the treatment itself, makes use of quality impressions, for example, computer-based 3-dimensional planning/design tools, such as ClinCheck® from Align Technology, Inc. However, inconsistent production of suitable quality impressions using current techniques can decrease the effectiveness or efficiency of many of the wide variety of techniques that make use of dental impressions.

As such, there is an increasing need for high quality dental impressions for the wide variety of procedures and techniques in dentistry and orthodontics. In turn, improved systems and methods are needed for producing more accurate and refined impressions of a patient's teeth, as well as impressions that can be more consistently and efficiently produced.

BRIEF SUMMARY OF THE INVENTION

The present invention relates to an improved dental impression tray and related methods. In one embodiment, the present invention includes a dental impression tray having a first portion and a second portion. The first portion is configured for receiving impression material from a source and can include a plurality of impression material distribution channels. The first portion further will include one or more impression material inlet ports in communication with the channels. The second portion is configured for receiving a patient's upper or lower teeth and will at least partial define a cavity shaped to receive the teeth during use. The second portion will include one or more walls, and can include a bottom connecting wall that couples the second portion to the first portion. The bottom connecting wall will include a plurality of openings that allow material introduced into the first portion to pass through the openings and into the second portion.

In another embodiment, the present invention includes a method of forming an impression of a patient's teeth. Such a method can include positioning an impression tray as described in the present disclosure in the patient's mouth, and introducing impression material into the tray. As further set forth herein, an impression tray of the present invention can include a first portion for receiving impressing material from a source and a second teeth receiving portion. According to a method of the present invention, introducing impression material into the tray can be done such that material enters channels of the first portion and passes into the second portion and around the patient's teeth. Once the impression material is sufficiently set, the tray and material can be removed from the patient's mouth for additional steps of making the impression.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

The present invention relates to an improved dental impression tray and related methods. The tray is designed to more evenly and efficiently flood impression material into the tray and around teeth positioned in the tray, thereby reducing impression inaccuracies, artifacts, air bubbles, and the like. The dental tray of the invention includes a first portion for receiving impression material and a second portion defining a cavity shaped to receive a patient's upper or lower teeth. In use, impression material is loaded into the first portion, where it then flows through the tray, into the teeth receiving portion and distributed to the patient's teeth positioned in the cavity. Rather than having a large, continuously open well, the impression material receiving portion of the tray includes a less-wasteful and more efficient network of distribution channels designed to guide the flow of material throughout the tray. These internal channels include a design and/or layout for improved flow and distribution of impression material. The configurations of the internal channels and associated outlet ports can be adapted to provide for even distribution of impression material by adjusting the relative resistance to the flow of the impression material between the inlet and a particular outlet delivery port by varying the size, shape, location, and distances between the inlet and a particular outlet delivery port, as well as by the size of the outlet port itself. In one embodiment, channels can be included and dimensioned or tapered, e.g., tapered from front to back, so as to accelerate downstream flow. Even distribution of impression material is further aided by providing left and right distributions channels, which are further divided to provide their own anterior and posterior distribution channels. The tray can be designed for coupling with a variety of impression material sources, and typically will conveniently be operable using a standard hand operated impression cartridge dispensing gun. The tray can be fabricated to have a solid or continuous one-piece construction, thereby providing a convenient, ready to use impression tray that does not necessarily require assembly or disassembly by the user.

Figure 1:
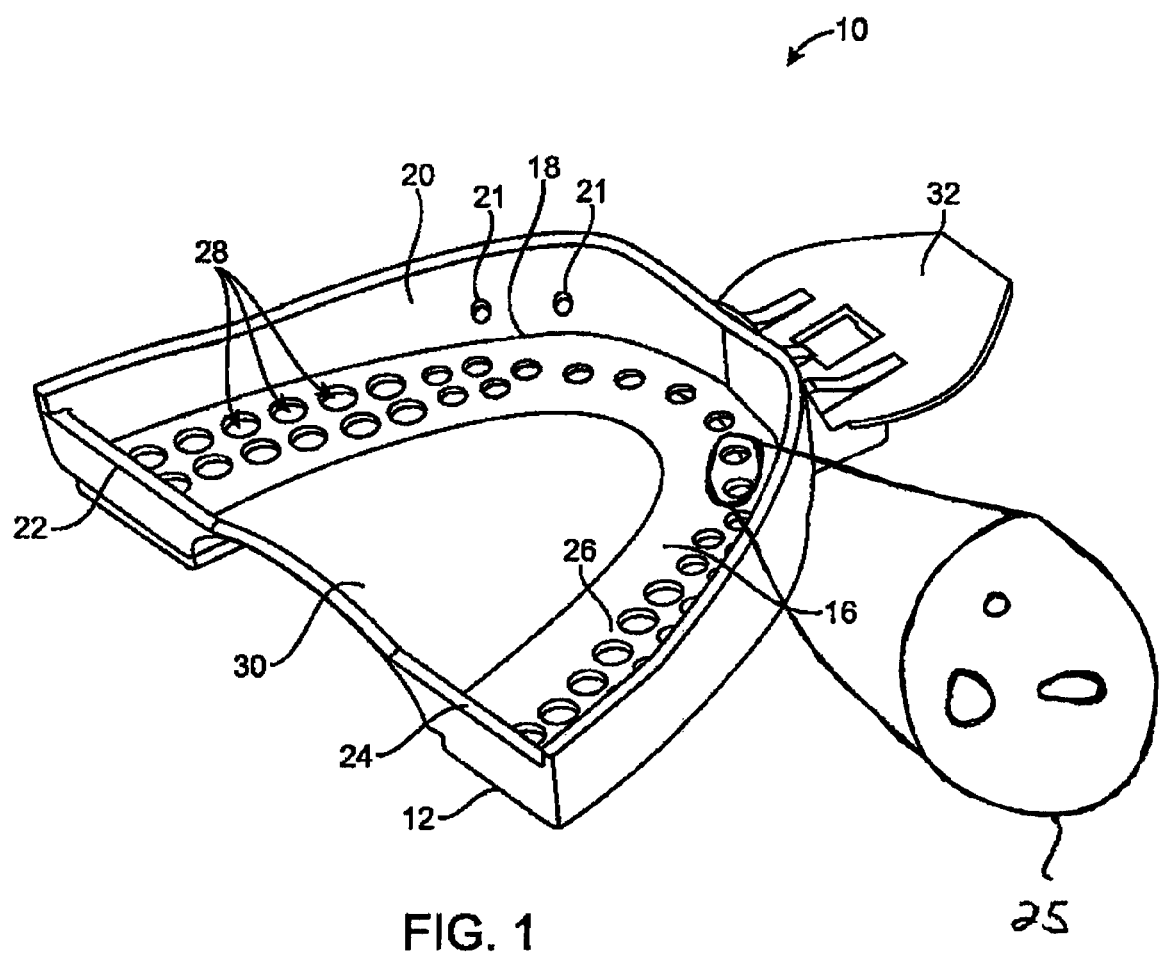
FIG. 1 illustrates an impression tray according to an embodiment of the present invention.

FIG. 1 illustrates an impression tray with a basic arch-shaped or U-shaped contour, according to an embodiment of the present invention. The impression tray 10 includes a portion 12 for initially receiving impression material from a source (not shown). The portion 12 includes an inlet port 14 and one or more channels that distribute introduced impression material throughout the portion 12. The tray 10 further includes a portion 16 shaped to receive a patient's teeth as well as impression material for the formation of a dental impression. The portion 16 will include one or more walls that define a cavity 18. In the illustrated embodiment a side wall 20 having a U shape at least partially defines cavity 18. The portion 16 further includes walls 22, 24 at the terminal ends of cavity 18, which during use can be positioned at the terminal portions of the patient's arch, e.g., proximate to a patient's molars, and can retain at least some of the impression material from flowing out of the cavity 18 and into the patient's mouth. Portion 16 will also include a wall 26 (e.g., connecting wall) that connects portions 12 and 16 and defines an at least partial barrier between the portions 12, 16. Wall 26 defines a plurality of openings 28 that allow material introduced into portion 12 to pass from portion 12 and into the cavity 18 of portion 16 by flowing through openings 28. Illustrated tray 10 further includes a wall 30 positioned in what would be the lingual portion of the patient's mouth during use. In other designs, wall 30 might have a structure more similar to wall 20, but sized smaller and defining an arch or U-shape along the lingual portion of the patient's arch. The illustrated tray provides a single piece construction where the portions 12 and 16 are connected in a sort of continuous manner to form a single piece or unit. The tray can optionally include a handle 32 or other structure that can be coupled to the tray 10, e.g., at the front of the tray as shown, and can provide structure for gripping and handling movement and/or positioning of the tray, e.g., positioning of the tray in the patient's mouth during use. A plurality of openings may include openings having different sizes or shapes, e.g., as conceptually illustrated with reference to expanded view 25.

Figure 2A:
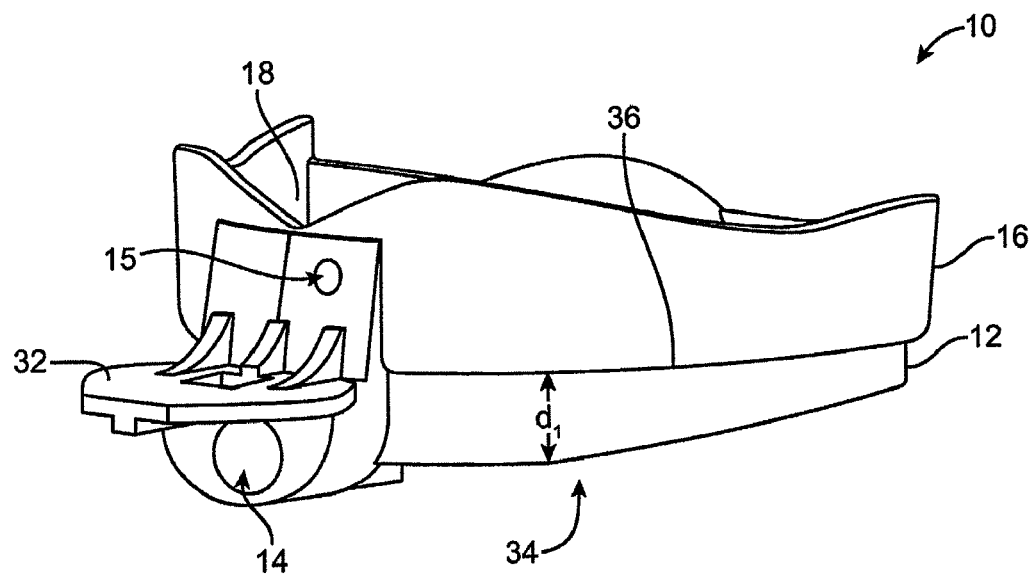
FIG. 2A shows a front/side view of the impression tray according to an embodiment of the present invention.

FIG. 2A illustrates a front side view of tray 10. Tray 10 includes portions 12 and 16, as discussed above. Portion 16 defines a teeth receiving cavity 18 as described. Portion 12 is designed for receiving impression material from a source through inlet port 14, which is introduced through inlet port 14 and distributed through channels (not shown) of portion 12. Portion 12 includes at least a side 34, which is illustrated as at least partially defining a bottom portion of the tray 10, and a side 36, which at least partially defines the interface of portion 12 with portion 16, e.g., at the bottom wall 26 of portion 16. In one embodiment, portion 12 can be vertically tapered where the distance between sides 34 and 36 decreases as moving from the front of the tray toward the back or terminal portion of the tray, as illustrated d1 and d2. Such a design can be selected, for example, so as to allow for more evenly timed distribution of impression material throughout the portion and the channels. For example, design can be selected to increase flow rate of impression material as the material moves from the front of the tray toward the back of the tray, thereby accounting for the decreased volume of impression material flowing from front to back as a result of the progressive exiting of impression material through openings 28.

Figure 3:
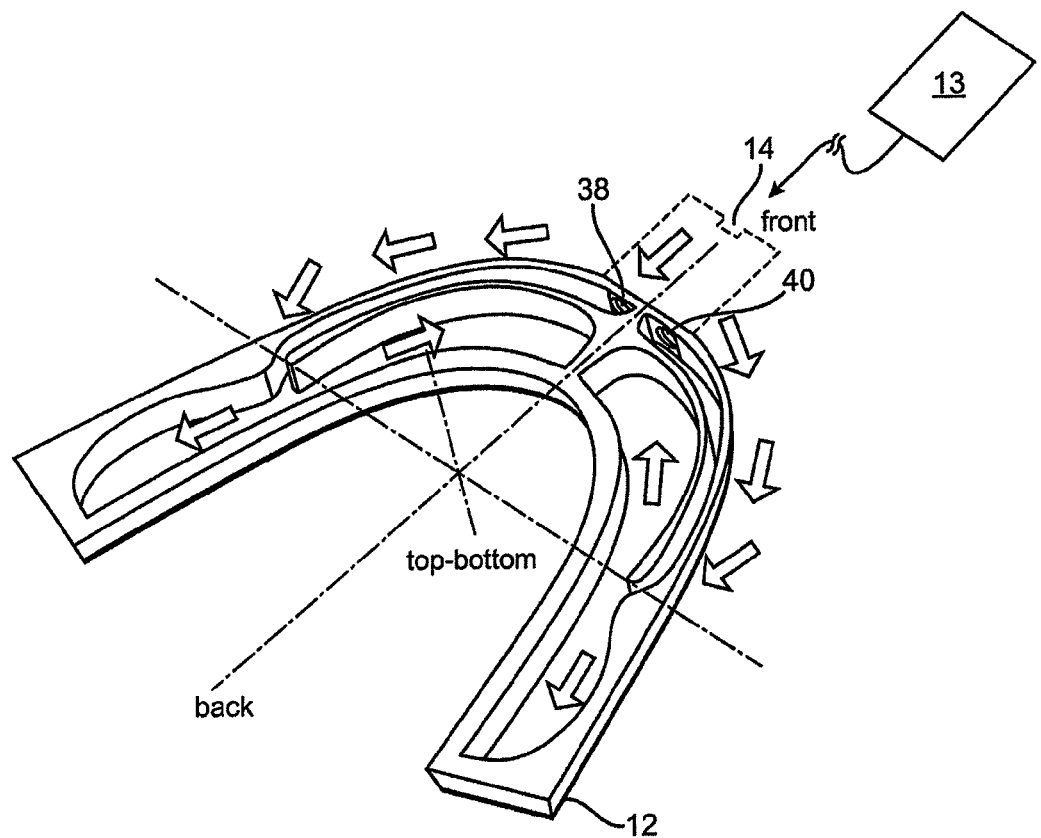
FIG. 3 illustrates a portion of an impression tray, according to an embodiment of the present invention, showing distribution channels.

FIG. 3 illustrates a cross-sectional view of portion 12 of the tray 10. Inlet ports 38 and 40 are further defined at a front portion of portion 12, with each port 38, 40 in communication distribution channels of portion 12. As illustrated, opposing symmetrical halves of portion 12 can include separate networks of distribution channels, with each network independently addressable by ports 38 and 40. A channel of the portion 12 can be tapered in width or longitudinally, or vary with regard to width or longitudinal distance between opposing sides at different locations within a given channel. Selecting channel dimensions in such a manner can allow differences in material flow at different locations or portions of the channel. For example, a channel can be tapered or constricted so as to allow more controlled or even flow of impression material in the channel. Arrows shown in FIG. 3 illustrate material flow within channels of the portion.

Figure 4:
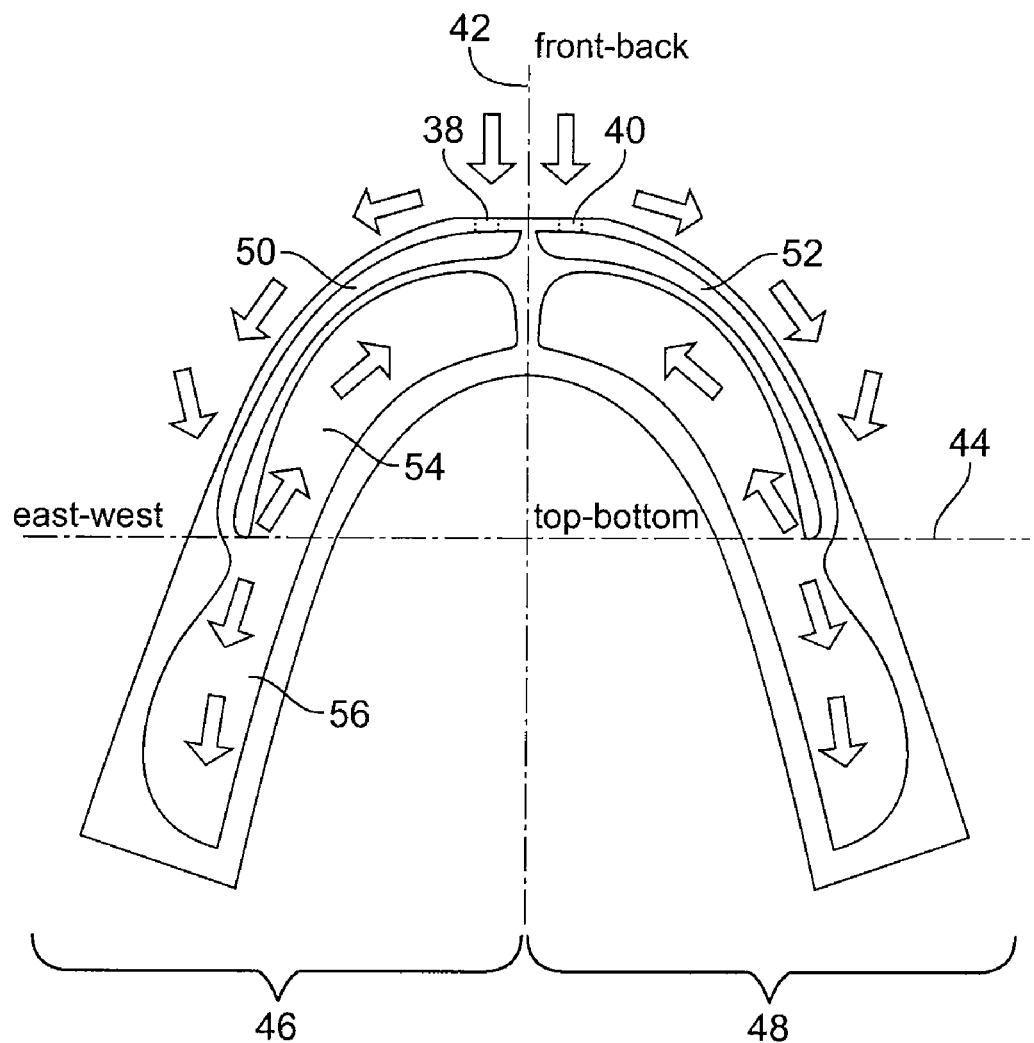
FIG. 4 shows a top view of a portion of an impression tray, according to an embodiment of the present invention, showing distribution channels.

FIG. 4 includes a cross-sectional top view of portion 12 of the tray 10. Axis 42 and axis 44 are shown in order to illustrate a quadrant-like design of portion 12 and distribution channels therein. This permits splitting the incoming material in half to defined regions, e.g., left 46 and right 48 regions of the tray as indicated by division along axis 42, by introduction of material through ports 38 and 40 connected to channels 50 and 52, respectively. Referring to side 46 of portion 12, downstream flow of material through channel 50 is sent approximately midway down side 46 of the tray to where channel 50 meets channels 54 and 56 where it is split again as material moves into channels 54 and 56, as indicated by the arrows. Similar arrangement of channels and designed flow of material introduced into the portion 12 through port 40 is illustrated in side 48. Such a design effectively creates four somewhat equal regions of portion 12 for impression material delivery. This quadrant-type design of portion 12 and arrangement of the distribution channels therein provides more even flow distribution of material through portion 12 and then into the cavity 18 of portion 16. Furthermore, the illustrated design reduces chances of interrupted flow or clogging within the tray by overwhelming a portion (e.g., channel, opening, etc.) with too much material.

During use, the tray is positioned or seated in a patient's mouth such that either the teeth of the patient's upper or lower arch are received by the cavity 18 of portion 16. The handle 32 allows the user to control movement and positioning. Impression material is introduced into the tray 10 through the one or more inlet ports 14. Material then enters the channels of the portion 12 and distributes through the portion in a controlled and desired manner.

From the inlet port 14, the material would pass through an internal distribution network of channels leading to openings defined by the bottom connecting wall 26 coupling the portion 12 and portion 16, and impression material flows around the teeth positioned in the cavity 18 of portion 16. The design and layout of the channels or distribution networks of portion 12 help ensure a smooth even flow of material through the tray 10, into the cavity 18, and around the teeth. By seating the teeth onto the tray first and then flooding the tray with impression material, the resulting impression is more complete. This will substantially reduce distortions that often occur with traditional tray insertion such as air bubbles, voids, drag marks, and incomplete capture.

Thus, a tray is seated in the patient's mouth and teeth positioned in the tray when at least the tray cavity is empty or prior to introduction of impression material into the tray cavity or even into any portion of the tray. An empty tray is easier to place correctly in the mouth compared to a tray with the teeth receiving cavity pre-filled with impression material prior to seating the teeth. Thus, the option of seating the tray with an empty cavity can allow more accurate alignment of the tray in a desired orientation left to right and front to back. Furthermore, any anatomical impingements can be more easily identified in advance by the attending doctor when seating an empty tray compared to one pre-filled with impression material. Once seated, the patient would be instructed to bite down onto the tray with their opposing jaw to temporarily hold it in place. Then, a source of the impression material is inserted into the inlet port of the tray and impression material such as, polyvinyl siloxane (PVS) is injected into the tray. An impression tray of the present invention can be configured for use with any variety of impression material sources, and can include designs suitable for use with material sources such as a standard impression cartridge hand operated dispenser or an electrically driven dispenser (e.g. dispenser 13, FIG. 3). Commercially available dispensers can be utilized in the present invention, including those available from a variety of different dental equipment manufactures, such as common brands including Aquasil by Dentsply Caulk, Exaflex by GC America, and Imprint by 3M ESPE. The material would flow through the specially designed interior network of distribution channels and delivered onto the surfaces of the teeth. Operation of an impression tray of the present invention can optionally include use of limited selected amount of impression material, such as enough material to surround the teeth, thereby providing a process that is less wasteful, gentler to the patient, and is far less likely to induce any unintentional tray movements. The resulting impression will be more complete and accurate, having less distortions or artifacts. The impression tray of the present invention further advantageously provides improved retention of impression material in the tray, as having a "built-in" undercarriage or material depository beneath the teeth receiving portion lends to extruded impression material being more firmly bonded to the tray.

The configuration of internal distribution channels in a portion of the tray adjacent to the portion defining a teeth receiving cavity reduces flow disparity in different portions of the tray, such as high flow forces on the front of the tray and low flow forces in the back of the tray, that can lead to uneven or undesirable deposition of impression material around the teeth. Instead, the current design reduces disparity or evens out flow forces and/or pressure gradients in different portions of the tray.

The ports or openings joining portions of the tray for delivering the impression material to the teeth (e.g., openings defined by a connecting wall) can be of various different shapes, sizes, and quantities to regulate the release of impression material into the main tray cavity. Openings are typically selected in both size and shape, as well as arrangement or positioning within the tray design, so as to work in unison with the channels and further ensure even outflow of impression material throughout the tray. In addition to the openings defined by a connecting wall as illustrated, e.g., in FIG. 1, openings or ports that allow impression material to pass into a teeth receiving cavity can be located or defined in other areas or structures of the impression tray. For example, an impression tray of the invention can include one or more ports or openings (e.g., side ports 21, FIG. 1) defined by a side wall of the portion defining a teeth receiving cavity. Thus walls can be hollowed (e.g., partially hollowed) or otherwise define a well, channel, etc. that permits passage of impression material from a first portion of the tray and into the teeth receiving cavity. Such openings or side ports can be in communication with the portion for receiving impression material from a source (e.g., first portion) and distribution channels thereof such that impression material is deliverable from the first portion, into the teeth receiving cavity, and to the patients teeth for making a dental impression. Furthermore, the openings/side ports can be positioned or defined at various locations on a wall, and positioning can be selected based on desired delivery location to the patient's teeth. For example, side ports can be positioned so as to deliver impression material to the side of the patient's teeth, at the gingival line, at specifically selected teeth of the patient's arch, and the like.

Figure 2B:
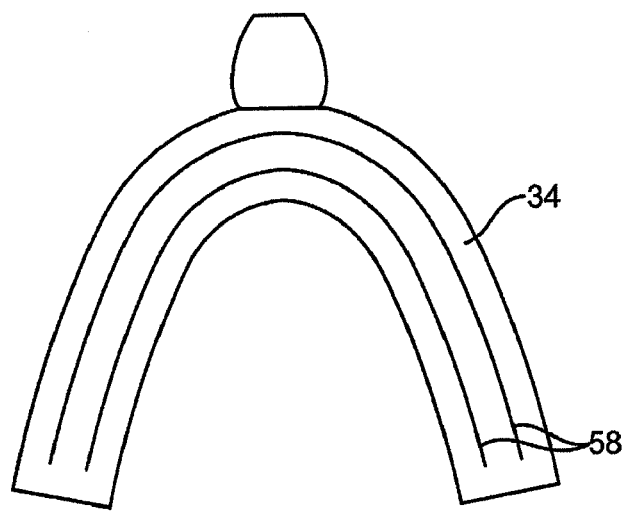
FIG. 2B shows a bottom view of the impression tray according to an embodiment of the present invention.

The tray can further include one or more teeth engaging structures positioned on the tray so as to engage a patient's teeth during use of the tray and help prevent or reduce undesired movement of the tray during use. In one embodiment shown in FIG. 2B, for example, a bottom surface 34 of a tray portion or exterior surface of the impression tray is designed with ridges 58 to be bitten onto by the opposing arch (or arch not being used for forming the impression) as a means of temporary anchorage during the impression process.

In one embodiment, a tray can further include a means for determining when the tray or portion thereof (e.g., teeth receiving cavity) has substantially filled with impression material. In one example, a channel can be provided that is in communication with an outlet 15 that is positioned at the front of the tray so that impression material passes through the outlet when a desired amount of impression material has been delivered to the tray. For example, a channel can be sent backwards into the tray handle to serve as a mechanism to indicate when the tray has been fully loaded, and can be accomplished by adjusting the travel distance of the channel until its inherent exit time matches the tray loading time.

As set forth above, a tray of the invention can include a substantially solid or continuous construction where a single-piece tray can be provided to the user. Fabrication of the tray can include fabrication of a single piece or fabrication of a plurality of pieces that are assembled and provided to a user as a single-piece construction. In some cases, an impression tray can include one or more removable components, such as one or more walls that can be removably attached/detached as desired by the user. For example, a tray can include a terminal wall at a terminal portion of a teeth receiving portion of the tray, with the wall being configured to restrict impression material from passing from the teeth receiving cavity and into the back of the patient's mouth. The terminal wall can be securely affixed to the tray or can be removably affixed. Various fabrication techniques can be employed in making an injection tray of the present invention, including: 1) separately injection molding in two parts with features allowing subsequent snap-together assembly; 2) separate injection molding of two parts followed by joining by sonic welding; and 3) building as one piece using three-dimensional rapid prototyping technology, followed by dissolving the required internal support structural supports to form the distribution channels. The tray can be used with the patient's mouth substantially closed, with only a small portion of the assembly, such as an injection nozzle, protruding outward.

Various types of impression materials can be utilized in conjunction with the tray of the invention, including various commercially available compositions. Since the design of the tray allows for fast loading and doesn't require preloading before seating the tray in the patient's mouth, the present design eliminates the need for a long working time associated with pre-mixing and loading steps. Therefore, a wider variety of impressing materials, including faster setting impression materials, can be used.

Impression trays and methods of the present invention can find use in a wide variety of dental or orthodontic techniques that make use of impressions or casting of a patient's teeth. In one embodiment, devices and techniques as described herein can be utilized, for example, in production, and/or associated use or treatment, of patient removable, incremental adjustment appliances, which can include a shell (e.g., polymeric shell) having teeth-receiving cavities that receive and resiliently reposition a patient's teeth. Such appliances, including those utilized in the Invisalign System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "align.com"). As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. Impressions can be utilized in various stages and aspects of treatment of a patient accordingly.

Although the invention has been described with reference to the above examples, it will be understood that modifications and variations are encompassed within the spirit and scope of the invention. Accordingly, the invention is limited only by the following claims along with their full scope of equivalents.

What is claimed is:

1. A dental impression tray, comprising:
   a first portion for receiving impression material from a source, the first portion defining an arch having a first region and a second region, the first region comprising a first plurality of impression material distribution channels, and the second region comprising a second plurality of impression material distribution channels, the impression tray first portion further comprising one or more impression material inlet ports in communication with the channels, wherein the first and second regions are separated so as to permit splitting of impressing material between the first and second regions; and
   a second portion defining an arch having a cavity shaped to receive a patient's upper or lower teeth, the second portion comprising one or more side walls and a bottom connecting wall coupling the second portion to the first portion, the bottom connecting wall defining a plurality of openings that allow material introduced into distribution channels of the first portion to pass through openings and into the second portion, wherein at least one of the channels of the first portion is shaped to promote substantially even distribution of impression material.

2. The dental impression tray of claim 1, wherein the tray comprises a continuous, single-piece construction.

3. The dental impression tray of claim 1, further comprising impression material deposited in a portion of the impression tray.

4. The dental impression tray of claim 1, wherein the plurality of openings includes openings having different sizes or shapes.

5. The dental impression tray of claim 1, wherein the geometry or positioning of the openings defined by the bottom connecting wall is configured to control entry of impression material into the teeth receiving cavity of the second portion.

6. The dental impression tray of claim 1, further comprising a teeth engaging structure positioned on a bottom side of the first portion that engages teeth of the patient's arch not being received by the cavity of the second portion during formation of an impression.

7. The dental impression tray of claim 6, wherein the teeth engaging structure is configured to reduce movement of the tray when positioned in the patient's mouth during impression formation.

8. The dental impression tray of claim 1, further comprising an impression material source coupled to the one or more impression material inlet ports.

9. The dental impression tray of claim 8, wherein the source comprises a hand operated dispensing gun or an electrically driven dispensing gun.

10. The dental impression tray of claim 1, further comprising a handle coupled to the front of the tray.

11. The dental impression tray of claim 1, the first portion further comprising a distribution channel in communication with an outlet positioned at the front of the tray so that impression material passes through the outlet when a desired amount of impression material has been delivered to the tray.

12. The dental impression tray of claim 1, further comprising one or more side ports defined by a side wall of the second portion, the one or more side ports in communication with the first portion so that impression material is deliverable to the patient's teeth.

13. The dental impression tray of claim 12, wherein the side ports are positioned to deliver impression material to a side or gingival line of the patient's teeth.

14. The dental impression tray of claim 1, further comprising a terminal wall at a terminal portion of the second portion and configured to restrict impression material from passing from the teeth receiving cavity and into the back of the patient's mouth.

15. The dental impression tray of claim 14, wherein the terminal wall is removable or non-removably affixed to the tray.

16. The dental impression tray of claim 14, wherein the terminal wall extends to a lingual or buccal side of the patient's arch.

17. A method of forming an impression of a patient's teeth, the method comprising:
   positioning an impressing tray in the patient's mouth, the dental impressing tray comprising:
   a) a first portion for receiving impression material from a source, the first portion defining an arch having a first region and a second region, the first region comprising a first plurality of impression material distribution channels, and the second region comprising a second plurality of impression material distribution channels, the impression tray first portion further comprising one or more impression material inlet ports fluidly connected to the channels, wherein the first and second regions are separated so as to permit splitting of impressing material between the first and second regions; and b) a second portion defining an arch having a cavity shaped to receive the patient's teeth, the second portion comprising one or more side walls and a bottom connecting wall coupling the second portion to the first portion, the bottom connecting wall defining a plurality of open ports that allow material introduced into distribution channels of the first portion to pass through openings and into the second portion, wherein at least one of the channels of the first portion is shaped to promote substantially even distribution of impression material; and introducing impression material into the tray through the one or more inlet ports such that material enters the channels of the first portion and passes through the openings of the connecting wall and into the second portion and around the patient's teeth.

18. The method of claim 17, wherein impression material substantially fills the channels of the first portion before passing through the openings of the connecting wall.

19. The method of claim 17, further comprising engaging a teeth engaging structure with teeth of the patient's arch not being received by the cavity of the second portion, the structure configured to reduce movement of the tray positioned in the patient's mouth.

20. The method of claim 17, wherein the teeth engaging structure includes a ridge positioned on a bottom side of the first portion.

21. The method of claim 17, wherein the impression material is delivered to the tray from an impression material source coupled to the one or more impression material inlet ports.

22. The method of claim 17, further comprising manipulating the tray in the patient's mouth using a handle coupled to the front of the tray.

23. The method of claim 17, further comprising detecting that an amount of impression material sufficient to obtain an impression has been delivered to the tray and discontinuing delivery of impression material to the tray.

24. The method of claim 23, the first portion of the tray comprising a distribution channel in communication with an outlet positioned at the front of the tray, and the detecting includes observing impression material passing through the outlet.

* * * * *